United States Patent [19]
Nicholson et al.

[11] Patent Number: 5,902,584
[45] Date of Patent: May 11, 1999

[54] ANTIBODIES WHICH BIND THE G-CSF RECEPTOR EXTRACELLUAR DOMAIN AND METHODS OF TREATMENT

[75] Inventors: Sandra E. Nicholson, Newport; Judith E. Layton, Clifton Hill; Andrew F. Wilks, Doncaster East; Andrew C. Oates, Carlton North; Ailsa G. Harpur, Mooroolbark, all of Australia

[73] Assignee: Ludwig Institute for Cancer Research, New York, N.Y.

[21] Appl. No.: 08/693,241

[22] PCT Filed: Feb. 8, 1995

[86] PCT No.: PCT/US95/01696

§ 371 Date: Jan. 21, 1997

§ 102(e) Date: Jan. 21, 1997

[87] PCT Pub. No.: WO95/21864

PCT Pub. Date: Aug. 17, 1995

[30] Foreign Application Priority Data

Feb. 8, 1994 [AU] Australia ............................... PM 3750

[51] Int. Cl.[6] .......................... A61K 39/395; C07K 16/00
[52] U.S. Cl. ..................................... 424/143.1; 530/388.22
[58] Field of Search ..................... 530/388.22; 424/143.1

[56] References Cited

U.S. PATENT DOCUMENTS 4,683,295  7/1987  Carson ..................................... 530/391

FOREIGN PATENT DOCUMENTS 9105046  4/1991  WIPO .

OTHER PUBLICATIONS

Sevier. E. Dale et al, Clin Chem, 27(11): 1797–1806, 1981.
Layton, J. E. et al, J. Biol Chem, 266(35): 23815–23823, Dec. 1991.

*Primary Examiner*—Susan A. Loring
*Attorney, Agent, or Firm*—Fulbright & Jaworski, LLP

[57] ABSTRACT

The invention relates to a composition comprising antibodies or binding portions thereof which bind to a naturally occurring or recombinant G-CSF receptor extracellular domain, and reduce tyrosine phosphorylation of a JAK molecule. The invention also relates to methods of using this composition for inhibiting or decreasing tyrosine phosphorylation of a JAK kinase and for inhibiting or decreasing G-CSF interaction with its receptor. Also described are antibodies which bind to a G-CSF receptor extracellular domain and which are produced by immunizing an animal with cells transfected with DNA encoding a G-CSF receptor.

28 Claims, 5 Drawing Sheets

ANTIBODIES WHICH BIND THE G-CSF RECEPTOR EXTRACELLUAR DOMAIN AND METHODS OF TREATMENT

FIELD OF THE INVENTION

The present invention relates generally to cytokine interactive molecules, such as antibodies and other immune reactive molecules, agonists and antagonists. The present invention also provides methods for assaying for the presence of cytokines or receptor associated proteins such as kinases and their function.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

BACKGROUND OF THE INVENTION

Granulocyte colony-stimulating factor (G-CSF) stimulates the proliferation and differentiation of neutrophil precursors via interaction with a specific cell surface receptor, the G-CSF receptor (G-CSF-R).

Although the G-CSF-R has been cloned (1) and is functionally active in several different cell types (2), little is known about the mechanism of signal transduction. The G-CSF-R is believed to consist of a single chain that is activated through ligand induced homodimerisation (3) as has been shown for the erythropoietin and growth hormone receptors (EPO-R, GH-R) (4). The G-CSF-R does not contain an intrinsic protein kinase domain (1) although tyrosine kinase activity seems to be required for transduction of the G-CSF signal (5). JAK kinases (6,7) are receptor-associated proteins which are rapidly phosphorylated after receptor activation. In particular, Tyk2 is phosphorylated following interferon α-receptor (IFNα-R) activation (8) and JAK2 following the binding of EPO (9), GH (10) and interleukin-3 (IL-3) (11) to their respective receptors.

In work leading up to the present invention, the inventors investigated early signal transduction events resulting from the association of G-CSF with its receptor and the role of JAK1 and JAK2.

In accordance with the present invention, antibodies were prepared to the extracellular domain of G-CSF-R. It has now been surprisingly discovered that G-CSF interaction with G-CSF-R is required for tyrosine phosphorylation of JAK kinases. The antibodies of the present invention now provide for a method of inhibiting G-CSF binding to its receptor and, by consequence, phosphorylation by JAK kinases. The present invention contemplates, therefore, a method for treating G-CSF related disease conditions or JAK1 and JAK2 phosphorylation associated disease conditions which result from G-CSF interaction with its receptor.

SUMMARY OF THE INVENTION

One aspect of the present invention is directed to a composition comprising antibodies or parts, fragments or derivatives thereof to G-CSF-R extracellular domain.

Another aspect of the present invention relates to antibodies to the composition defined above.

Yet another aspect of the present invention contemplates a method for inhibiting, reducing or otherwise decreasing tyrosine phosphorylation of JAK1 or JAK2 in a mammal, said method comprising administering to said mammal a binding effective amount of an antibody or a part, fragment or derivative thereof interactive with G-CSF-R extracellular domain.

Still yet another aspect of the present invention contemplates a method for inhibiting, reducing or otherwise decreasing G-CSF interaction with G-CSF-R in a mammal, said method comprising administering to said mammal, a binding effective amount of an antibody or part, fragment or derivative thereof interactive with G-CSF-R extracellular domain.

In still yet another aspect of the present invention, there is provided agonists and antagonists to G-CSF-R.

BRIEF DESCRIPTION OF THE FIGURES

AML-193 cells were incubated with rhG-CSF (100 ng/ml) for the times indicated (minutes) and lysed. Tyrosine phosphorylated proteins were immunoprecipitated with antiphosphotyrosine antibody 4G10 (αPY), Upstate Biotechnology Inc. (UBI). The immunoprecipitated proteins were separated by sodium dodecyl sulfate-polyacrylamide gel electrophoresis (SDS-PAGE) 6% w/v gel and analysed by Western blot using either JAK1 antiserum (M7) (αJAK1, JAK2 antiserum (UBI) (αJAK2) or TYK2 antiserum, Santa Cruz Inc. (αTYK2). The mobilities of the pre-stained molecule weight markers are shown on the left.

CHO-6A11 cells were incubated with rhG-CSF for the times indicated (minutes) and lysed. JAK1 and JAK2 proteins were immunoprecipitated using purified JAK1 antiserum (M7) (left panel) and JAK2 antiserum (UBI) (right panel). Immunopreciptates were separated using SDS/6% w/v PAGE and subjected to Western blot analysis using antiphosphotyrosine antibody 4G10 (αPY) (upper panel).

CHO-6A11 cells were incubated with rhG-CSF for the times indicated (minutes) and lysed. JAK1 and JAK2 proteins were immunoprecipitated using purified JAK1 antiserum (M7) (left panel) and JAK2 antiserum (UBI) (right panel). Immunoprecipitates were washed and suspended in an equal volume of kinase buffer (20) containing [γ-$^{32}$P]ATP (0.25 $\mu$Ci/ml) for 30 minutes at room temperature. Immunoprecipitates were analysed by SDS/6% w/v PAGE. The gels were treated with 1 mol/L KOH 55° C. for two hours to remove phosphoserine and phosphothreonine. Radioactive bands were visualised with IMAGEQUANT software on a PhosphorImager system (Molecule Dynamics).

AML-193 cells were incubated with rhG-CSF (100 ng/ml) (+) or medium (−) for 10 minutes. Cells were lysed and G-CSF-R proteins immunoprecipitated using the monoclonal antibody LMM741. Following SDS/6% w/v PAGE analysis, proteins were electrophoretically transferred to nitrocellulose and immunoblotted with either JAK2 antiserum (M7) (left panel) for JAK2 antiserum (UBI) (right panel).

AML-193 cells were incubated with either G-CSF, GM-CSF or IL-6 at 100 ng/ml or medium (control) for 10 minutes and immunoprecipitated with antiphosphotyrosine antibody 4G10 (αPY). Immunoprecipitated proteins were separated by SDS/6% w/v PAGE and analysed by Western blot with either JAK1 antisrum (M7) (αJAK1), JAK2 antiserum (UBI) (αJAK2) or TYK2 antiserum (Santa Crus) (αTYK2). The mobilities of the pre-stained molecular weight markers are shown on the left.

DETAILED DESCRIPTION OF THE PREFERRED EMBODIMENTS

The present invention relates generally to antibodies to G-CSF-R. Preferably, the antibodies are directed to the extracellular domain of G-CSF-R and more particularly a recombinant form of this molecule. The present invention is also directed to parts, fragments or derivatives of such antibodies which still interact with the G-CSF-R. The antibodies of the present invention are generally in isolated or purified form meaning that a composition comprises at least 25%, more preferably at least 35%, even more preferably at least 45–50%, still more preferably at least 60–70% and even still more preferably at least 80–95% of the antibodies as determined by weight, immunoreactivity or other convenient means. Alternatively, the antibodies may be present in the form of isolated culture supernatant, tissue extract, serum or whole blood or ascites fluid.

Preferably, the G-CSF-R is of mammalian origin such as from a human, livestock animal (e.g. cow, horse, sheep, goat or donkey), laboratory test animal (e.g. mouse, rat or rabbit), companion animal (e.g. dog or cat) or captive wild animal (e.g. dingo, fox, wild boar or kangaroo). The most preferred receptors are of human and laboratory test animal origin (e.g. murine species).

Where the antibodies are polyclonal antibodies, they may be generated in any convenient host including a human, livestock animal, companion animal or captive wild animal as exemplified above. Where the antibodies are monoclonal antibodies, they may be prepared in any convenient hybridoma such as of murine (i.e. mouse or rat) origin.

The receptor used to generate the antibodies may be the whole receptor such as in purified, partially purified or isolated form including in the form of isolated membrane preparations. The receptor may also be produced by recombinant procedures or synthetic procedures or a combination thereof. In a particularly preferred embodiment, a fragment of the receptor is used which, in an even more preferred embodiment, is fused to a suitable carrier or marker molecule such as FLAG protein or alkaline phosophatase (AP). Glutathione-S-transferase (GST) may also be used.

According to this preferred embodiment, there is provided an antibody or part, fragment or derivative thereof interactive with a non-full length G-CSF-R fused to a carrier molecule. The non-full length portion of the receptor acts as a hapten and is or forms part of the extracellular domain. Preferably, the carrier molecule is FLAG or AP. Alternatively, the carrier molecules is GST.

The resulting fusion molecule may then be used to generate polyclonal or monoclonal antibodies which may undergo immunoadsorbent procedures to provide a composition of substantially, for example, extracellular domain-reactive receptor antibodies.

The terms "antibody" or "antibodies" are used herein in their broadest sense and include parts, fragments, derivatives, homologues or analogues thereof, peptide or non-peptide equivalents thereof and fusion molecules between two or more antibodies or between an antibody and another molecule. The antibodies or other immunointeractive molecules may also be in recombinant or synthetic form.

Accordingly, the present invention contemplates mutants and derivatives of the antibodies which interact with G-CSF-R extracellular domains. Mutants and derivatives of such antibodies include amino acid substitutions, deletions and/or additions. Furthermore, amino acids may be replaced by other amino acids having like properties, such as hydrophobicity, hydrophilicity, electronegativity, bulky side chains, interactive and/or functional groups and so on. Glycosylation variants and hybrid antibodies are also contemplated by the present invention.

Amino acid substitutions are typically of single residues; insertions usually will be of the order of about 1–10 amino acid residues; and deletions will range from about 1–20 residues. Deletions or insertions preferably are made in adjacent pairs, i.e: a deletion of 2 residues or insertion of 2 residues.

The amino acid variants referred to above may readily be made using peptide synthetic techniques well known in the art, such as solid phase peptide synthesis and the like, or by recombinant DNA manipulations. Techniques for making substitution mutations at predetermined sites in DNA having known sequence are well known, for example through M13 mutagenesis. The manipulation of DNA sequences to produce variant proteins which manifest as substitutional, insertional or deletional variants are well known in the art.

Other examples of recombinant or synthetic mutants and derivatives of the antibodies of the present invention include single or multiple substitutions, deletions and/or additions to any molecule associated with the ligand such as carbohydrates, lipids and/or proteins or polypeptides. Naturally occurring or altered glycosylated forms of the subject antibodies are particularly contemplated by the present invention.

Amino acid alterations to the subject polypeptide contemplated herein include insertions such as amino acid and/or carboxyl terminal fusions as well as intrasequence insertions of single or multiple amino acids. Generally, insertions within the amino acid sequence will be smaller than amino or carboxyl terminal fusions, of the order of about 1 to 4 residues. Insertional amino acid sequence variants are those in which one or more amino acid residues are introduced into a predetermined site in the protein. Deletional variants are characterised by the removal of one or more amino acids from the sequence. Substitutional variants are those in which at least one residue in the sequence has been removed and a different residue inserted in its place. Such substitutions may be made in accordance with Table 1.

TABLE 1

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Pro; Val |

TABLE 1-continued

| Original Residue | Exemplary Substitutions |
|---|---|
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The terms "analogues" and "derivatives" also extend to any functional chemical equivalents of the antibodies characterised by their increased stability and/or efficacy in vivo or in vitro. The terms "analogue" and "derivatives" further extend to any amino acid derivative of the antibodies as described above.

Antibody analogues contemplated herein include, but are not limited to, modifications to side chains, incorporation of unnatural amino acids and/or derivatising the molecules and the use of crosslinkers and other methods which impose conformational constraints on the antibodies. Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbomoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides could be conformationally constrained by, for example, incorporation of $C_\alpha$ and $N_+$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention, therefore, extends to amino acid and/or chemical analogues of the subject antibodies having the identifying characteristics of being interactive with the extracellular domain of G-CSF-R.

Accordingly, reference herein to an antibody includes the naturally occurring molecule, recombinant, synthetic and analogue forms thereof and to any mutants, derivatives and human and non-human homologues thereof including amino acid and glycosylation variants.

The antibodies of the present invention may be used to develop a new range of therapeutic and diagnostic agents. For example, the antibodies or fragments or derivatives thereof may act as antagonists and be useful, for example, in the treatment of G-CSF related disease conditions which result from G-CSF interaction with its receptor, including JAK family phosphorylation related disorders (e.g. some cancers and tumours). They may also be used for screening for agonists useful, for example, where G-CSF interaction (or JAK1 or JAK2 phosphorylation) is to be promoted. Normal, abnormal or mutant receptor structure or receptor expression may also be determined through immunoreactivity studies.

According to this latter embodiment, there is contemplated a method of detecting a G-CSF-R on a cell in a biological sample, said method comprising contacting said sample with an antibody capable of binding to the extracellular domain of said G-CSF-R immobilised to a solid support for a time and under conditions sufficient for an antibody G-CSR-R complex to form and then detecting the presence of said complex.

In one preferred method, the complex is detected by contacting the complex with a second antibody against the first mentioned antibody with the second antibody being labelled with a reporter molecule. Alternatively, the first antibody itself is labelled with a reporter molecule.

The first and second antibodies may be polyclonal or monoclonal and both are obtainable by immunisation of a suitable animal with the interactive molecule and either type is utilisable in the assay. The methods of obtaining both types of sera are well known in the art. Polyclonal sera are less preferred but are relatively easily prepared by injection of a suitable laboratory animal with an effective amount of immunointeractive molecule, or antigenic parts thereof, collecting serum from the animal, and isolating specific antibodies by any of the known immunoadsorbent techniques.

Although antibodies produced by this method are utilisable in virtually any type of assay, they are generally less favoured because of the potential heterogeneity of the product.

The use of monoclonal antibodies in the above immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495–499, 1975; *European Journal of Immunology* 6: 511–519, 1976).

The presence of a G-CSF-R may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are particularly useful in the present invention. A number of variations of the sandwich assay technique exist, and all are intended to be encompassed by the present invention. Briefly, in a typical forward assay, an antibody is brought into contact with a biological sample comprising cells potentially carrying G-CSF-R. After a suitable period of incubation, for a period of time sufficient to allow formation of an antibody G-CSF-R complex, a second antibody specific to the complexed antibody, labelled with a reporter molecule capable of producing a detectable signal, is then added and incubated allowing sufficient time for the formation of a tertiary complex. Any unreacted material is washed away, and the presence of the second antibody bound to the first antibody is determined by observation of a signal produced by the reporter molecule. The results may either be qualitative, by simple observation of the visible signal, or may be quantitated by comparing with a control sample containing known amounts of hapten. Variations on the forward assay include using a first antibody (against G-CSF-R) labelled with a reporter molecule. In addition, the antibodies or cells carrying G-CSF-R may be immobilised onto a solid support.

Suitable solid supports include glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing molecules to the polymer.

"Reporter molecule", as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the immunointeractive molecule or an antibody thereto generally by means of glutaraldehyde or periodate. As will be readily recognised, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a fluorescent product rather than the chromogenic substrates noted above. Generally, the enzyme-labelled antibody is added to the immunointeractive molecule-receptor complex, allowed to bind, and then the excess reagent is washed away. Alternatively, an enzyme labelled immunointeractive molecule is used. A solution containing the appropriate substrate is then added to the tertiary complex. The substrate will react with the enzyme linked to the antibody/immunointeractive molecule, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. Immunofluoresence and EIA techniques are both very well established in the art and are particularly useful for the present method. However, other reporter molecules, such as radioisotope, chemiluminescent or bioluminescent molecules, may also be employed.

By detecting G-CSF-R by the procedures, aberrant receptors may be discerned thus providing a useful screening procedure for potential disease conditions.

The present invention also provides a pharmaceutical composition comprising an effective amount of antibodies capable of binding or otherwise associating with the extracellular domain of G-CSF-R and one or more pharmaceutically acceptable carriers and/or diluents. The active ingredients of a pharmaceutical composition comprising the antibodies are contemplated to exhibit excellent therapeutic activity, for example, in the treatment of G-CSF disease conditions such as some cancers, in an amount which depends on the particular case. For example, from about 0.5 $\mu$g to about 20 mg per kilogram of body weight per day of antibody may be administered. Dosage regima may be adjusted to provide the optimum therapeutic response. For example, several divided doses may be administered daily or the dose may be proportionally reduced as indicated by the exigencies of the therapeutic situation.

The active compound may be administered in a convenient manner such as by the oral, intravenous (where water soluble), intramuscular, subcutaneous, intranasal, intradermal or suppository routes or implanting (eg using slow release molecules).

Depending on the route of administration, the active ingredients which comprise the immunointeractive molecules may be required to be coated in a material to protect said ingredients from the action of enzymes, acids and other natural conditions which may inactivate said ingredients. In order to administer the immunointeractive molecules by other than parenteral administration, they will be coated by, or administered with, a material to prevent its inactivation. For example, the immunointeractive molecules may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water emulsions as well as conventional liposomes.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the antibodies are suitably protected as described above, the active, compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 10 $\mu$g and 2000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 $\mu$g to about 2000 mg. Expressed in proportions, the active compound is generally present in from about 0.5 μg to about 2000 mg/ml of carrier. In the case of compositions containing supplementary active ingredients, the dosages are determined by reference to the usual dose and manner of administration of the said ingredients.

In a most preferred embodiment, the antibodies used in a pharmaceutical composition are antibodies or mutants or derivatives thereof. Most preferably, the antibodies are monoclonal antibodies.

The present invention is further described by reference to the following non-limiting example.

EXAMPLE

To generate a model system for analysing signal transduction by the human G-CSR-R, CHO-K1 cells were transfected with the human G-CSF-R (CHO-6A11). The cell line CHO-6A11 was generated by transfection with the pEE6.HCMV.GS expression vector (12) carrying a full length cDNA encoding the G-CSF-R. These cells expressed approximately 60,000 receptors per cell (as determined by binding of $I^{125}$G-CSF). Monoclonal and polygonal antibodies to the G-CSF-R were produced to enable detection of receptor-associated proteins. Polyclonal rabbit antiserum, designated R55, was generated by immunisation with a pGEX/G-CSF-R bacterial fusion protein encompassing the haemopoietin receptor domain. A BamH1 fragment of the receptor cDNA encoding amino acids 17-345 was inserted into the BamH1 site of PGEX-1 (13). The monoclonal antibody to the G-CSF-R, LMM174 was raised against CHO-6A11 cells.

Figure 1:
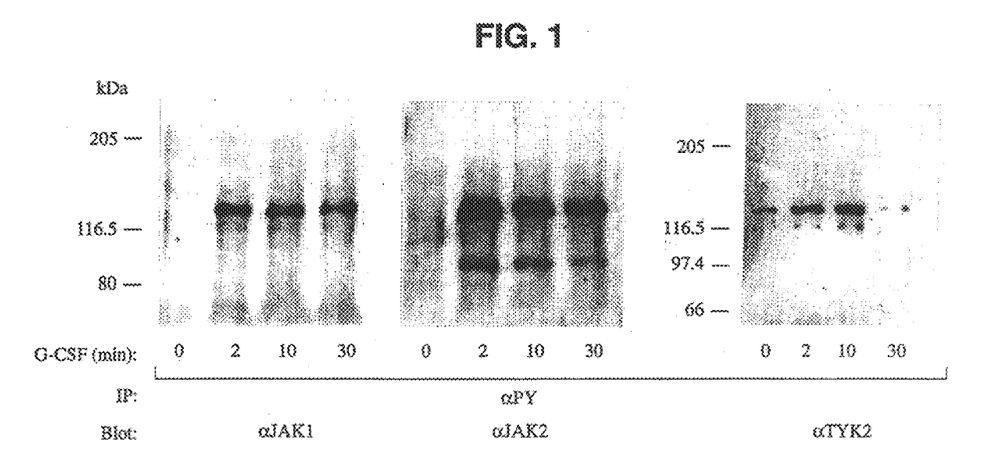
FIG. 1 is a photographic representation showing tyrosine phosphorylation of JAK kinases in response to G-CSF (AML-193 cells).

The monoclonal antibody LMM741 and rabbit serum R55 detected the receptor in cell lysates from CHO-6A11 and the human monocytic leukaemic cell line AML-193 (14) (FIG. 1A). Two protein of apparent molecular mass 130 and 110 kDa were detected in CHO-6A11 lysates (FIG. 1A, lane D) and were not present in untransfected CHO-K1 cell lysates (FIG. 1A, lane C) or when non-immune rabbit serum was used (FIG. 1A, lanes A and B). Three proteins of apparent molecule mass 145, 135 and 115 kDa were detected in AML-193 cells (FIG. 1A, lane E). The different sized proteins observed are likely to be due to differently glycosylated forms of the receptor (2). AML-193 cells proliferated in response to G-CSF whereas CHO-6A11 cells did not (FIG. 1B).

Figure 2A:
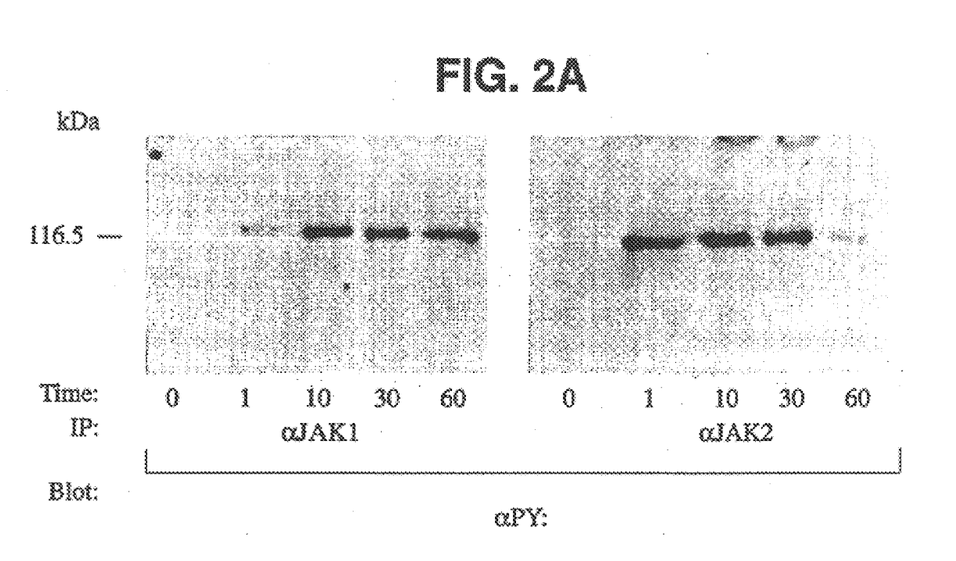
FIG. 2A is a photographic representation showing tyrosine phosphorylation of JAK1 and JAK2 in response to G-CSF (CHO-6A11 cells).

Stimulation of CHO-6A11 cells with G-CSF induced a tyrosine phosphorylated band of 130 kDa which was immunoprecipitated by antiserum to JAK1 (M7) (FIG. 2A). M7 was generated by immunisation with a pGEX/JAK1 bacterial fusion protein spanning the first kinase-like domain of JAK1 (amino acids 576–825) (8). When compared with JAK2 antiserum, M7 detects a protein which migrates slower on SDS-PAGE than JAK2, suggesting that it is specific for JAK1, despite the close homology of domain 1 between JAK1 and JAK2 (15).

Figure 2B:
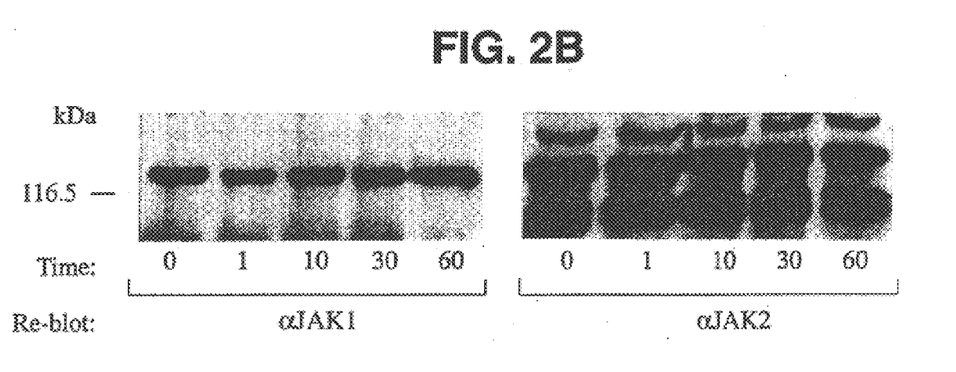
FIG. 2B is a photographic representation showing tyrosine phosphorylation of JAK1 and JAK2 in response to G-CSF (CHO-6A11 cells). Subsequent to the procedure described in FIG. 2A, the nitrocellulose was stripped of antisera and re-probed using M7 and JAK2 antiserum (lower panel) demonstrating equal sample loading in each lane. The mobilities of the pre-stained molecular weight markers are shown on the left.

Phosphorylation of JAK1 was also observed by immunoprecipitation with M7 and immunoblotting with anti-phosphotyrosine (FIG. 2B). When this blot was stripped and re-probed with M7, the result (FIG. 2B, lower panel), showed that there was equal sample loading in all lanes. Tyrosine phosphorylation of JAK1 was observed after 2 minutes of G-CSF stimulation, was maximal between 10 and 20 minutes and still evident, although decreasing, after 60 minutes.

Tyrosine phosphorylation of JAK1 in response to G-CSF was also observed in the AML-193 cells (FIG. 2C). Increased levels of phosphotyrosine have proved to be an excellent index of the involvement of particular protein tyrosine kinases in signal transduction pathways (15). The involvement of JAK1 in intracellular events triggered by G-CSF was thus strongly indicated by these data.

Figure 3:
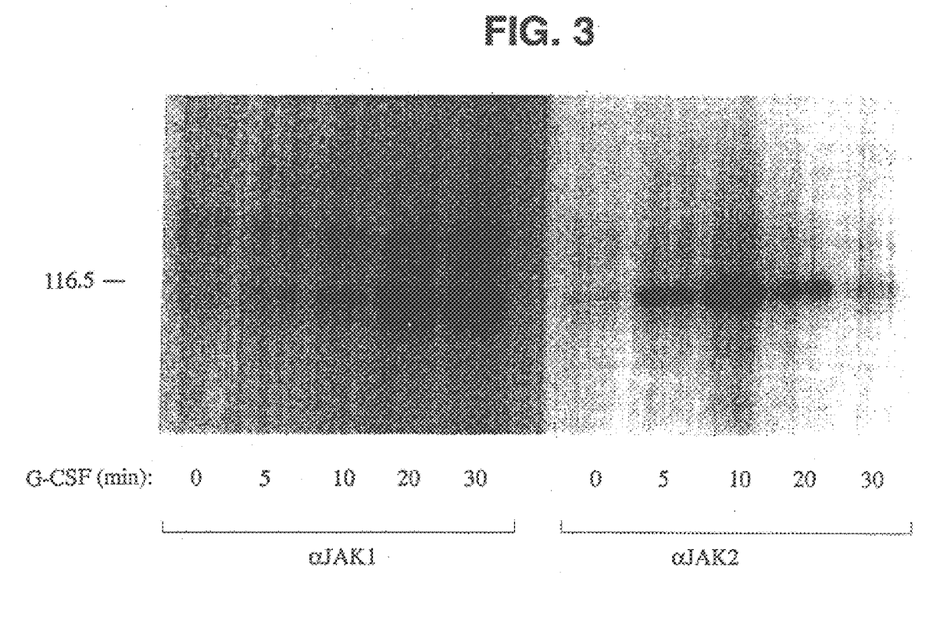
FIG. 3 is a photographic representation showing JAK1 and JAK2 autokinase activity in CHO-6A11 cells.

An in vitro kinase assay (11) was used to test whether the increased tyrosine phosphorylation of JAK1 correlated with an increase in intrinsic kinase activity. When incubated with [$\gamma$-$^{32}$P]ATP, JAK1 showed an increased capacity to autophosphorylate in response to G-CSF stimulation (FIG. 3A). A higher molecular weight band of unknown identity was also phosphorylated. The kinase activity appeared to be maximal at 30 minutes. Phosphoamino acid analysis from kinase assay samples of 0 and 30 minutes after G-CSF stimulation confirmed that JAK1 was phosphorylated on tyrosine residues (FIG. 3B). Some increase in phosphorylation on serine residues was also observed. This is in contrast to the observation that JAK2 incorporates $^{32}$P into tyrosine and threonine residues (9). Thus, the elevated kinase activity of JAK1 upon activation of CHO-6A11 cells by G-CSF underscores the likely involvement of this molecule in G-CSF-mediated signal transduction.

Figure 4:
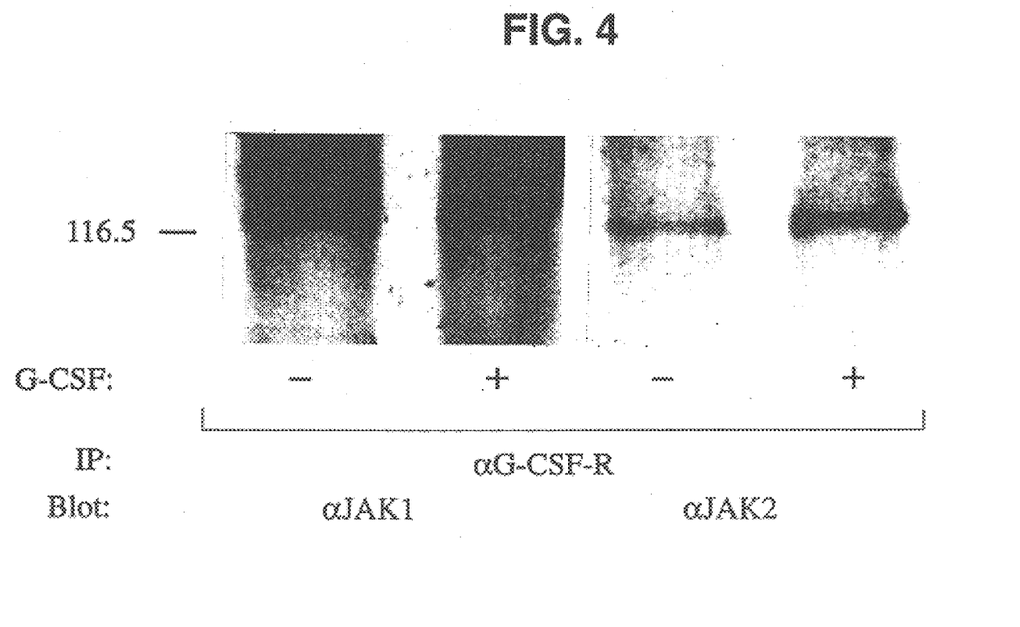
FIG. 4 is a photographic representation showing association of JAK1 and JAK2 with the G-CSF receptor.

To determine whether JAK1 is physically associated with the G-CSF-R, a receptor immunoprecipitate was analysed by blotting with M7. JAK1 co-immunoprecipitated with the G-CSF-R both before and after G-CSF treatment of CHO-6A11 cells (FIG. 4, lanes A and B). This band was not observed when G-CSF-R immunoprecipitates were blotted with M7 pre-immune serum. The amount of JAK1 co-immunoprecipitate remained constant for at least 20 minutes (not shown) and appeared to be a relatively small percentage of total cytoplasmic JAK1 (FIG. 4, lanes C and D). Receptor immunoprecipitates also shown in vitro kinase activity corresponding to a 130 kDa protein.

Figure 5:
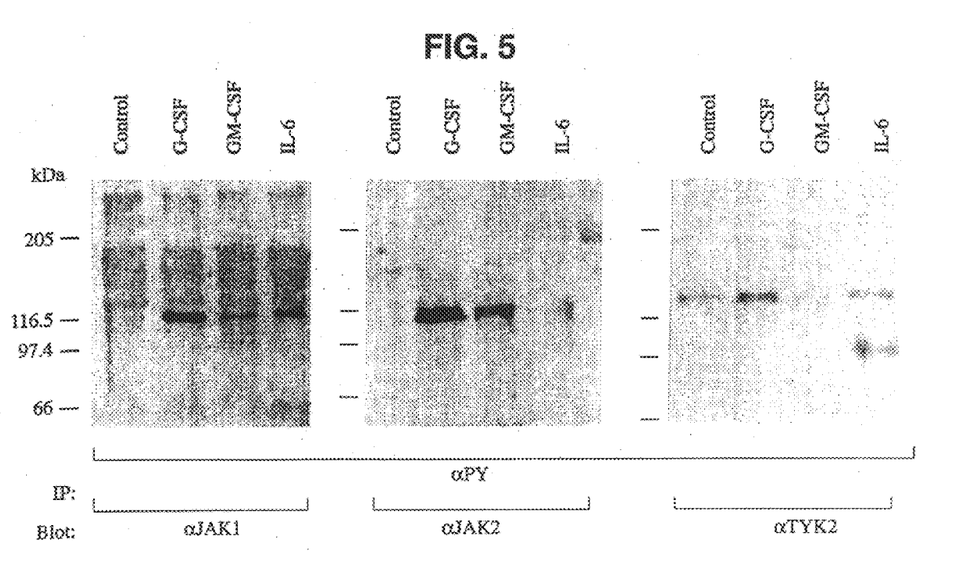
FIG. 5 is a photographic representation showing that different cytokines result in tyrosine phosphorylation of specific JAK kinases in AML-193 cells.

Stimulation of CHO-6A11 cells with G-CSF also resulted in phosphorylation of the G-CSF-R on tyrosine within 2 minutes of G-CSF stimulation (FIG. 5). The phosphorylated receptor migrated at a higher apparent molecular mass (150 and 135 kDa) that the two main bands detected by LMM741 and R55. Differential migration of phosphorylated protein has been observed with other proteins, for example, STAT91 (16) and middle sized tumour antigen (17). Phosphorylation of the murine G-CSF-R in a transfected hemopoietic cell line (32D) has also been detected recently by Pan et al. (18).

The G-CSF-R shows considerable homology with gp130 (46.3% amino acid similarity) (2), signal transducing component of the IL-6, oncostin M, LIF, CNTF and II-11 receptors. Of interest, two of the three highly conserved regions of homology between gp-130 and the G-CSF-R have been shown to be necessary for signal transduction, most notably a 99 amino acid region of the cytoplasmic domain (2). Consistent with the notion that this homology indicates similar function, it has been recently observed JAK1 association with gp-130 following IL-6 and LIF stimulation.

The data presented here are strongly suggestive of an important role for JAK1 in G-CSF receptor signal transduction pathways. The co-precipitation of G-CSF and JAK1 demonstrates a close association between these molecules. Furthermore, phosphorylation of both within two minutes of G-CSF binding makes it likely that JAK1 is the kinase responsible for G-CSF-R phosphorylation. Recent reports indicate that JAK1 is interdependent with at least one other JAK family kinase in signaling pathways for IFNα and IFNγ receptors.

Although the CHO-4A11 system is an artificial one, it is clear that AML-193 cells, which proliferate in response to. G-CSF, share the same JAK1 response (FIG. 2C). This suggests that these observations can also be applied to signal transduction from the native G-CSF-R.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. R. Fukunaga, Y. Seto, S. Mizushima, S. Nagata, *Proc. Natl. Acad. Sci. U.S.A.* 87: 8702 (1990); Larsen et al., *J. Exp. Med.* 172: 1559 (1990); R. Fukunaga, E. Ishizaka-Ikeda, Y. Seto, S. Nagata, *Cell* 61: 341 (1990).
2. R. Fukunaga, E. Ishizaka-Ikeda, C. Pan, Y. Seto, S. Nagata, *EMBO* 10: 2855 (1991).
3. R. Fukunaga, E. Ishizaka-Ikeda, S. Nagata, *J. Biol. Chem.* 265: 14008 (1990); E. Ishizaka-Ikeda, R. Fukunaga, W. I. Wood, D. V. Goeddel, S. Nagata, *Proc. Natl. Acad. Sci. USA* 90: 123 (1993).
4. S. Watawich et al., *Proc. Natl. Acad. Sci. USA* 89: 2140 (1992); G. Fuh et al., *Science* 256: 1677 (1992).
5. R. J. Isfort and J. N. Ihle, *Growth Factors* 2: 213 (1990).
6. A. F. Wilks et al., *Mol. Cell. Biol.* 11: 2057 (1991).
7. A. G. Harpur et al., *Oncogene* 7: 1347 (1992).
8. L. Velazquez, M. Fellous, G. R. Stark, S. Pellegrini, *Cell* 70: 313 (1992).
9. B. A. Witthuhn et al., *Cell* 74: 227 (1993).
10. L. S. Argetsinger et al., *Cell* 74: 0.237 (1993).
11. O. Silvennoinen et al., *Proc. Natl. Acad. Sci. USA* 90: 8429 (1993).
12. P. Stephens and M. Cockett,*Nucleic Acids Res.* 17: 7110 (1989); M. Cockett et al., *Biotechnology* 8: 662 (1990).
13. D. B. Smith and K. S. Johnson, *Gene* 67: 31 (1988).
14. B. Lange et al., *Blood* 70: 192 (1987).
15. A. F. Wilks, *Adv. Cancer Res.* 60: 43 (1993).
16. K. Shuai, C. Schinder, V. R. Prezioso, J. E. Darnell, *Science* 258: 1808 (1992).
17. L. Perez et al., *Proc. Natl. Acad. Sci. USA* 90: 8113 (1993).
18. C.-X. Pan, R. Fukunaga, S. Yonehara, S. Nagata, *J. Biol. Chem.* 268, In Press (1993).
20. Nicholson et al., *Proc. Natl. Acad. Sci. USA* 91: 2985 (1994).

We claim:

1. A composition comprising antibodies or binding portions thereof, wherein said antibodies or binding portions bind to a G-CSF receptor extracellular domain and reduce tyrosine phosphorylation of a JAK molecule thereby.

2. The composition of claim 1 wherein the G-CSF receptor extracellular domain is in recombinant form.

3. The composition of claim 1 wherein the antibodies are polyclonal antibodies.

4. The composition of claim 1 wherein the antibodies are monoclonal antibodies.

5. The composition of claim 1 wherein the antibodies are labeled with a reporter molecule.

6. An antibody which binds to the antibodies or binding portions of claim 1.

7. The antibody according to claim 6, labeled with a reporter molecule.

8. A method for inhibiting or decreasing tyrosine phosphorylation of a JAK kinase in a mammal comprising administering to said mammal the composition of claim 1.

9. The method of claim 8 wherein the antibodies bind a recombinant form of the G-CSF receptor extracellular domain.

10. The method of claim 8 where the antibodies are polyclonal antibodies.

11. The method of claim 8 where the antibodies are monoclonal antibodies.

12. The method of claim 8 wherein the mammal is a human, livestock animal, companion animal or laboratory test animal.

13. The method of claim 12 wherein the mammal is a human or murine species.

14. A method for inhibiting or decreasing G-CSF interaction with G-CSF receptor in a mammal comprising administering to said mammal the composition of claim 1.

15. The method of claim 14 wherein the antibodies bind a recombinant form of G-CSF receptor extracellular domain.

16. The method of claim 14 where the antibodies are polyclonal antibodies.

17. The method of claim 14 where the antibodies are monoclonal antibodies.

18. The method of claim 14 wherein the mammal is a human, livestock animal, companion animal or laboratory test animal.

19. The method of claim 14 wherein the mammal is a human or murine species.

20. Antibodies or binding portions thereof which bind to a G-CSF receptor extracellular domain, said antibodies produced by immunizing an animal with cells transfected with DNA encoding a G-CSF receptor.

21. The antibodies of claim 20 wherein the antibody binds G-CSF receptor extracellular domain in recombinant form.

22. The antibodies of claim 20 wherein said antibodies are polyclonal antibodies.

23. The antibodies of claim 20 wherein said antibodies are monoclonal antibodies.

24. A method of treating a condition resulting from G-CSF interaction with its receptor comprising administering a pharmaceutically effective amount of antibodies of claim 20.

25. The method of claim 24 wherein the antibodies bind a recombinant form of G-CSF receptor extracellular domain.

26. The method of claim 24 where the antibodies are polyclonal antibodies.

27. The method of claim 24 where the antibodies are monoclonal antibodies.

28. The method of claim 24 wherein the mammal is a human, livestock animal, companion animal or laboratory test animal.

* * * * *